US008636695B2

(12) United States Patent
Cluff et al.

(10) Patent No.: US 8,636,695 B2
(45) Date of Patent: Jan. 28, 2014

(54) ASSEMBLY METHOD FOR CATHETER WITH BLOOD CONTROL

(75) Inventors: Ken Cluff, Saratoga Springs, UT (US); William G. Moulton, West Jordan, UT (US); Edward G. Henderson, III, Draper, UT (US); Jeff McMurray, Murray, UT (US); Kenneth B. Lindstrom, Provo, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 64 days.

(21) Appl. No.: 13/431,781

(22) Filed: Mar. 27, 2012

(65) Prior Publication Data

US 2012/0184912 A1    Jul. 19, 2012

Related U.S. Application Data

(62) Division of application No. 12/877,494, filed on Sep. 8, 2010.

(51) Int. Cl.
A61M 5/178    (2006.01)

(52) U.S. Cl.
USPC ................. 604/167.01; 604/165.03

(58) Field of Classification Search
USPC .............. 604/167.01, 164.08, 167.02, 165.03
See application file for complete search history.

(56) References Cited

U.S. PATENT DOCUMENTS

| 4,387,879 A | 6/1983 | Tauschinski |
| 4,449,693 A | 5/1984 | Gereg |
| 4,758,225 A | 7/1988 | Cox et al. |
| 4,842,591 A | 6/1989 | Luther |
| 4,874,377 A | 10/1989 | Newgard et al. |
| 4,917,668 A | 4/1990 | Haindl |
| 4,935,010 A | 6/1990 | Cox et al. |
| 5,041,097 A | 8/1991 | Johnson |
| 5,053,014 A | 10/1991 | Van Heugten |
| 5,062,836 A | 11/1991 | Wendell |
| 5,064,416 A | 11/1991 | Newgard et al. |
| 5,084,023 A | 1/1992 | Lemieux |
| 5,085,645 A | 2/1992 | Purdy et al. |
| 5,108,374 A | 4/1992 | Lemieux |
| 5,127,905 A | 7/1992 | Lemieux |
| 5,154,703 A | 10/1992 | Bonaldo |

(Continued)

FOREIGN PATENT DOCUMENTS

| CA | 2133053 A1 | 3/1995 |
| CN | 101210849 A1 | 7/2008 |
| WO | WO 99/34849 | 7/1999 |

OTHER PUBLICATIONS

Silva, Elson, Email Regarding "Respecting Hydrology Science and IP Rights—US Pat. Application 20110130728," pp. 1-6, Jun. 2, 2011.

Primary Examiner — Nicholas Lucchesi
Assistant Examiner — Melissa A Snyder
(74) Attorney, Agent, or Firm — Jeanne Lukasavage; Craig Metcalf; Kirton McConkie

(57) ABSTRACT

A system and method for assembling a catheter device, wherein a septum actuator is positioned within the lumen of a catheter adapter to provide a pathway through a septum component, an introducer needle being inserted through the septum via the septum actuator thereby preventing damage to the septum, the septum actuator thereafter being withdrawn from the septum and positioned within a rearward chamber of the catheter adapter lumen.

6 Claims, 14 Drawing Sheets

(56) References Cited

U.S. PATENT DOCUMENTS

| | | |
|---|---|---|
| 5,156,596 A | 10/1992 | Balbierz et al. |
| 5,234,410 A | 8/1993 | Graham et al. |
| 5,295,969 A | 3/1994 | Fischell et al. |
| 5,330,435 A | 7/1994 | Vaillancourt |
| 5,350,363 A | 9/1994 | Goode et al. |
| 5,352,205 A | 10/1994 | Dales et al. |
| 5,405,323 A | 4/1995 | Rogers et al. |
| 5,456,675 A | 10/1995 | Wolbring et al. |
| 5,487,728 A | 1/1996 | Vaillancourt |
| 5,520,666 A | 5/1996 | Choudhury et al. |
| 5,549,566 A | 8/1996 | Elias et al. |
| 5,549,577 A | 8/1996 | Siegel et al. |
| 5,575,769 A | 11/1996 | Vaillancourt |
| 5,613,663 A | 3/1997 | Schmidt et al. |
| 5,651,772 A | 7/1997 | Arnett |
| 5,657,963 A | 8/1997 | Hinchliffe et al. |
| 5,697,915 A | 12/1997 | Lynn |
| 5,738,144 A | 4/1998 | Rogers |
| 5,749,861 A | 5/1998 | Guala et al. |
| 5,806,831 A | 9/1998 | Paradis |
| 5,817,069 A | 10/1998 | Arnett |
| 5,911,710 A | 6/1999 | Barry et al. |
| 5,954,698 A | 9/1999 | Pike |
| 5,967,490 A | 10/1999 | Pike |
| 6,039,302 A | 3/2000 | Cote, Sr. et al. |
| 6,077,244 A | 6/2000 | Botich et al. |
| 6,117,108 A | 9/2000 | Woehr et al. |
| 6,171,287 B1 | 1/2001 | Lynn et al. |
| 6,273,869 B1 | 8/2001 | Vaillancourt |
| 6,485,473 B1 | 11/2002 | Lynn |
| 6,575,960 B2 | 6/2003 | Becker et al. |
| 6,595,981 B2 | 7/2003 | Huet |
| 6,699,221 B2 | 3/2004 | Vaillancourt |
| 6,740,063 B2 | 5/2004 | Lynn |
| 6,883,778 B1 | 4/2005 | Newton et al. |
| 7,008,404 B2 | 3/2006 | Nakajima |
| 7,126,303 B2 * | 10/2006 | Farritor et al. ........... 318/568.12 |
| 7,347,839 B2 | 3/2008 | Hiejima |
| 7,396,346 B2 | 7/2008 | Nakajima |
| 7,470,254 B2 | 12/2008 | Basta et al. |
| 7,736,339 B2 | 6/2010 | Woehr et al. |
| 7,914,494 B2 | 3/2011 | Hiejima |
| 2003/0105431 A1* | 6/2003 | Howell ................... 604/164.08 |
| 2006/0085004 A1 | 4/2006 | Chien |
| 2006/0155245 A1 | 7/2006 | Woehr |
| 2006/0264833 A1 | 11/2006 | Moulton |
| 2007/0083162 A1 | 4/2007 | O'Reagan et al. |
| 2008/0039796 A1 | 2/2008 | Nakajima |
| 2008/0108944 A1 | 5/2008 | Woehr et al. |
| 2010/0204675 A1 | 8/2010 | Woehr et al. |

* cited by examiner

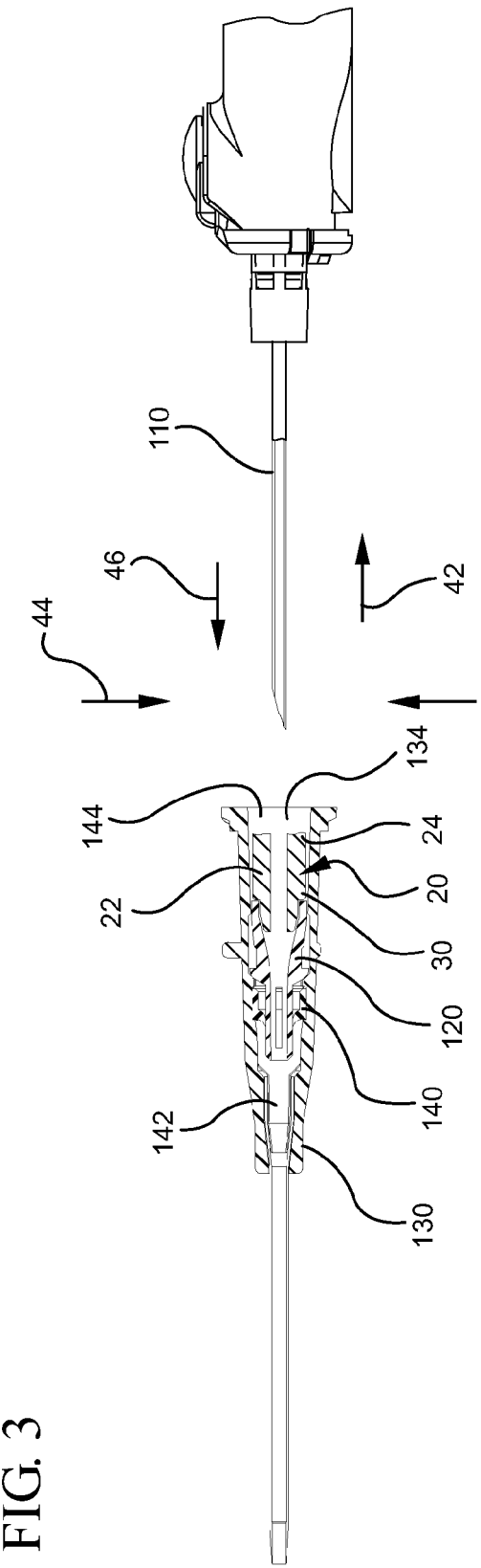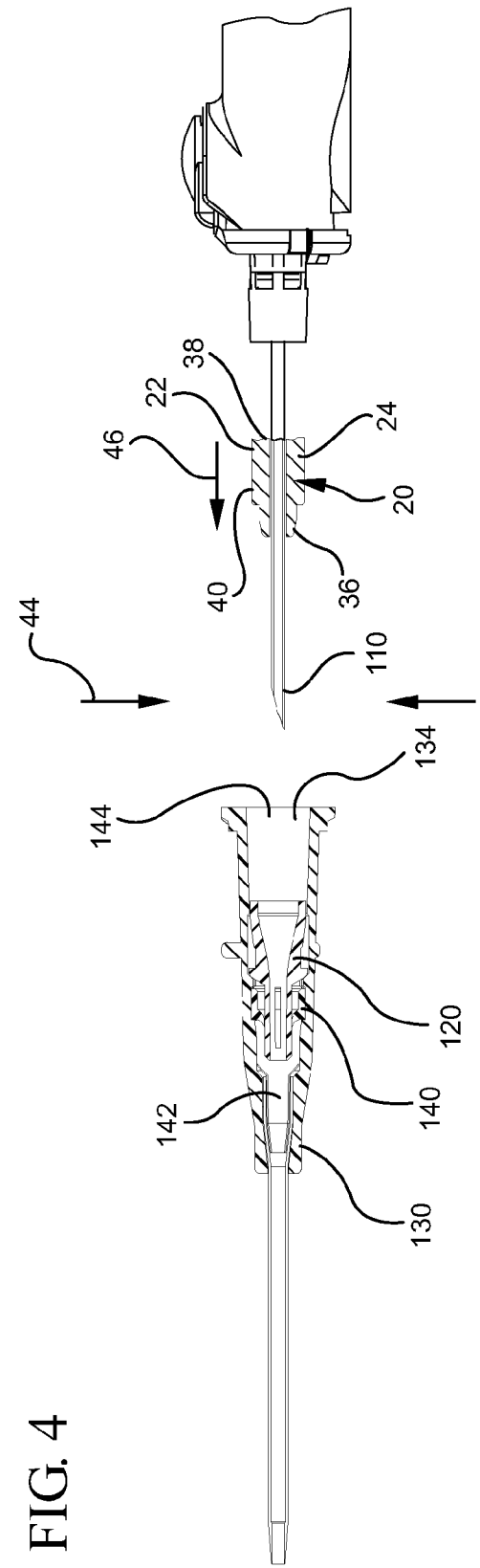

ASSEMBLY METHOD FOR CATHETER WITH BLOOD CONTROL

RELATED APPLICATIONS

This application is a divisional application of U.S. application Ser. No. 12/877,494, filed on Sep. 8, 2010, entitled ASSEMBLY METHOD FOR CATHETER WITH BLOOD CONTROL, and is incorporated herein.

BACKGROUND OF THE INVENTION

The current invention relates to an assembly method for a catheter device having a septum for blood control. In particular, the invention relates to a method and system whereby a catheter device is assembled such that the introducer needle is positioned within the catheter without causing damage to the septum of the catheter device.

Catheters are commonly used for a variety of infusion therapies. For example, catheters are used for infusing fluids, such as normal saline solution, various medicaments, and total parenteral nutrition into a patient, withdrawing blood from a patient, as well as monitoring various parameters of the patient's vascular system.

Catheters are commonly introduced into the vasculature of a patient as part of an intravenous catheter assembly. The catheter assembly generally includes a catheter hub, which supports the catheter, the catheter hub being coupled to a needle hub which supports an introducer needle. The introducer needle is extended and positioned within the catheter such that a beveled portion of the needle is exposed beyond a tip of the catheter. The beveled portion of the needle is used to pierce the skin of the patient to provide an opening whereby to insert the needle in the vasculature of the patient. Following insertion and placement of the catheter, the introducer needle is removed from the catheter thereby providing intravenous access to the patient.

For some catheter devices, a septum is additionally placed within the catheter hub so as to limit or control the passage of fluids through the catheter assembly. For example, following insertion of the catheter into a patient, blood from the patient will flow through the catheter and into the catheter hub. By placing a septum within the catheter hub, the septum acts as a barrier to prevent or control blood flow through the catheter hub. Upon removal of the introducer needle from the catheter, the septum may also act to remove excess blood from the outer surface of the needle.

For some catheter devices, a septum actuator is further placed within the catheter hub, whereby a user may advance the actuator through the septum to enable fluid to bypass the septum. The septum actuator may include a probe-like structure having a front end for piercing or otherwise bypassing the septum, and a tail end whereby the user contacts and advances the actuator through the septum. In some catheter devices, the septum actuator is positioned within a rearward portion of the catheter adapter prior to insertion of the catheter. Following insertion of the catheter and removal of the introducer needle, the septum actuator is advanced through the septum thereby providing fluid communication between the rearward portion of the catheter adapter and the vasculature of the patient.

Prior to using the catheter device, the various components of the device are assembled so as to provide a functional device. The method by which the catheter device is assembled is selected to correctly position the various components while preventing the occurrence of damage or misalignment of the components in the assembled device. Additionally, the assembly method is selected to provide high throughput and quality control.

Accordingly, there is a need in the art for assembly methods and systems that provide high throughput and highly reproducible catheter devices incorporating various components. Furthermore, there is a need in the art to provide a efficient assembly method that reduces or prevents damage or misalignment of the various components in an assembly catheter device. Such a method and system is disclosed herein.

BRIEF SUMMARY OF THE INVENTION

In order to overcome the limitations discussed above, the present invention relates to an assembly method for a catheter device having a septum for blood control. In particular, the invention relates to a method and system whereby a catheter device is assembled such that the introducer needle is positioned within the catheter without causing damage to the septum of the catheter device.

In some implementations, a catheter device is assembled by first providing a catheter adapter having a proximal opening, a distal opening, and a lumen extending therebetween. A catheter is then swaged into the distal opening of the catheter adapter, such that a lumen of the catheter and the lumen of the catheter adapter are in fluid communication. A septum is then insertedly positioned within the catheter adapter lumen thereby dividing the lumen into a forward chamber and a rearward chamber.

The catheter device is further assembled by insertedly positioning a septum actuator through the septum via a clamping device. For example, in some implementations a clamp device is used to access and insertedly position the septum actuator within the septum. The clamping device generally includes an opened position a closed position, and a middle position whereby the clamping device is capable of gripping the septum actuator and an introducer needle of the catheter device.

In some implementations, the clamping device is first used to grip and advance the septum actuator through the septum. The clamping device then releases the septum actuator and grips the introducer needle. The clamping device then advances into the catheter adapter lumen such that a beveled tip of the needle safely bypasses the septum via the septum actuator and into the forward chamber.

Following insertion of the needle tip, clamping device is then moved to the opened position whereby the clamping device releases the needle and secures the inner surface of the septum actuator. The clamping device is then withdrawn in a proximal direction thereby removing the septum actuator from the septum, such that the septum actuator is entirely positioned within the rearward chamber. The clamping device is then moved to the middle position such that the clamping device is free from contacting either the septum actuator or the needle. While in the middle position, the clamping device is withdrawn from the lumen and removed entirely from the catheter device. The needle is then completely advanced within the catheter lumen thereby completing the assembly of the catheter device.

In some implementations, a clamping device is provided whereby to manipulate the position of the septum actuator relative to the catheter adapter lumen. Additionally, a separate manipulator is provided whereby to grip and position the needle within the catheter adapter lumen, the septum actuator, and the septum components of the catheter device. Generally, the clamping device comprises an open position and a closed position. In the open position, an outer surface of the clamping device contacts an inner surface of the septum actuator. Conversely, in the closed position the clamping surface is concentrically positioned within the septum actuator, but does not contact the actuator. In some implementations, the clamping device further comprises a central opening through which the needle is inserted. The diameter of the central opening is such that when the clamping device is in the closed position, the needle may be freely moved through the central opening via the separate manipulator.

Further, in some implementations a stationary clamp is provided whereby to secure the needle hub and introducer needle in a stationary position. Additionally, a first manipulator is provided whereby to grip and position the septum actuator relative to the positions of the introducer needle and the catheter adapter. A second manipulator is further provided whereby to grip and position the catheter adapter relative to the positions of the introducer needle and the septum actuator.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 3 is a cross-sectioned view of a catheter device and assembly system undergoing a method of assembly following the step of advancing the septum actuator through the septum in accordance with a representative embodiment of the present invention.

FIG. 4 is a cross-sectioned view of a catheter device and assembly system undergoing a method of assembly prior to the step of advancing the introducer needle through the septum via the septum actuator in accordance with a representative embodiment of the present invention.

DETAILED DESCRIPTION OF THE INVENTION

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
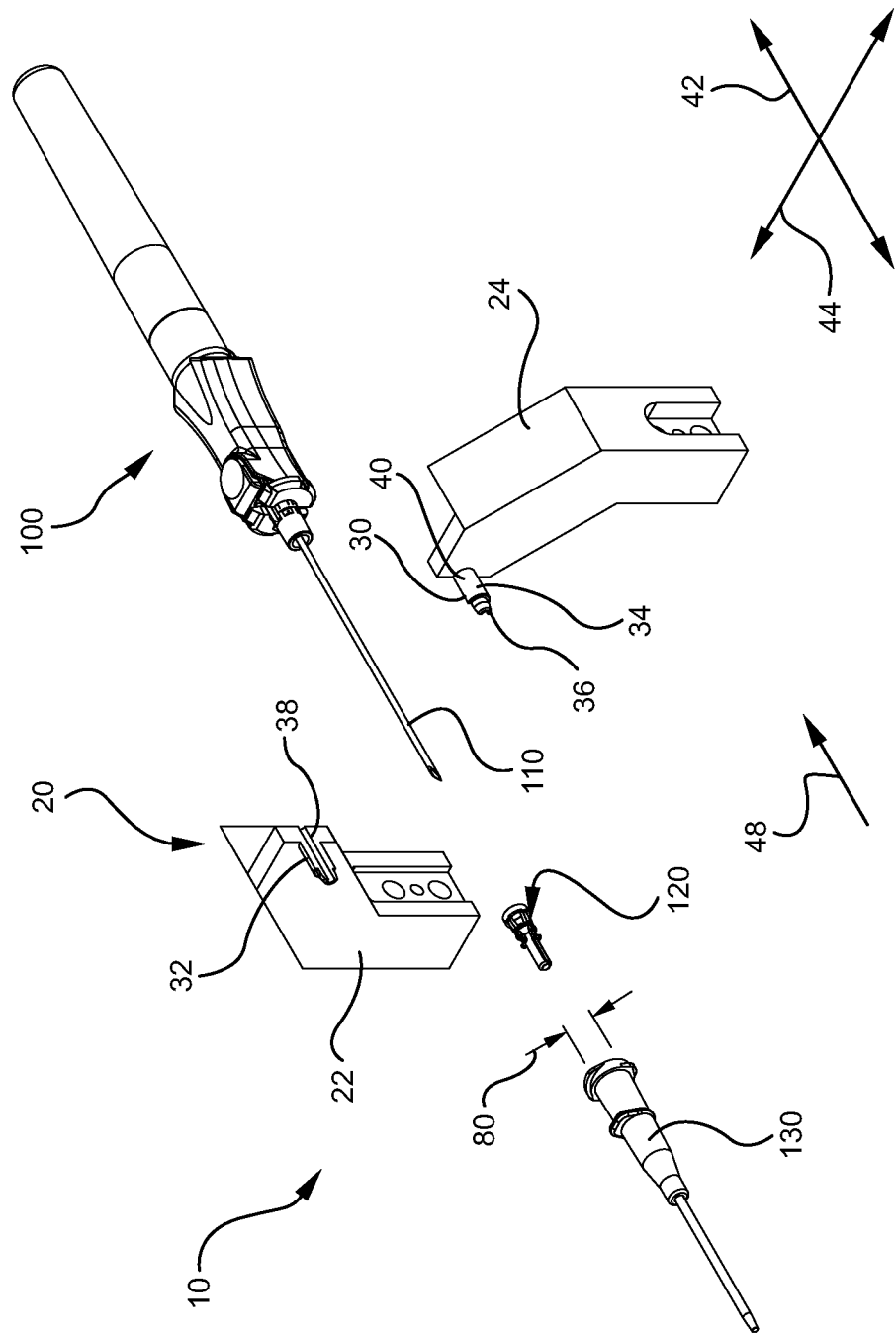
FIG. 1 is an exploded perspective view of a catheter device and assembly system in accordance with a representative embodiment of the present invention.

Referring now to FIG. 1, a catheter device assembly system 10 is shown. In some embodiments, system 10 comprises a clamp 20 having a first opposing arm 22 and a second opposing arm 24. Opposing arms 22 and 24 are configured to include a post 30 having a first half 32 associated with the first arm 22 and a second half 34 associated with the second arm 24.

In some embodiments, post 30 further comprises a groove or inner surface 38 for receiving and grasping the outer surface of an introducer needle 110 of catheter device 100. Post 30 further comprises a first outer surface 36 having an outer diameter for insertedly receiving septum actuator 120. In some embodiments, outer surface 36 is outwardly tapered in a proximal direction 48 so as to accommodate coupling between post 30 and septum actuator 120. In some embodiments, post 30 further comprises a second outer surface 40 having an outer diameter that is greater than the diameter of first outer surface 36, but slightly less than an inner diameter 80 of catheter adapter 130. As such, second outer surface 40 acts as a guide to coaxially center post 30 within catheter adapter 130 during assembly. Further, any component coupled to, or gripped by post 30 is likewise coaxially centered within catheter adapter 130 upon insertion therein.

In some embodiments, clamp 20 is mechanically connected to an automation system of actuators and gears (not shown) whereby clamp 20 is selectively repositioned along an x-axis 42 and a y-axis 44. In some embodiments, the automation system further comprises a computer and computer readable software whereby to provide an assembly program for the catheter device 100. Movement along the x-axis 42 and y-axis 44 is provided to enable clamp 20 to grasp and position the various catheter components within the catheter adapter 130 during assembly of catheter device 100.

Figure 2:
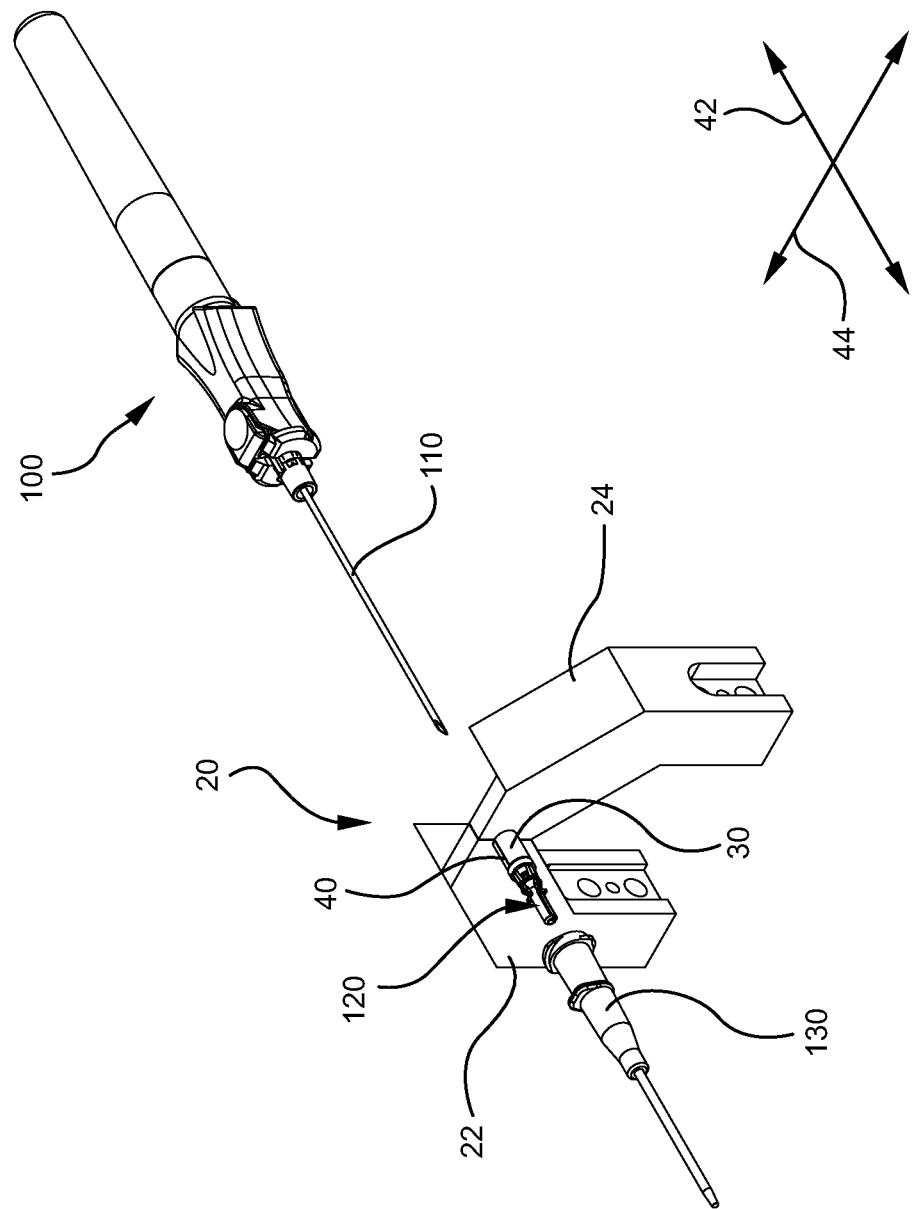
FIG. 2 is a perspective view of a catheter device and assembly system undergoing a method of assembly in accordance with a representative embodiment of the present invention.

For example, in some steps of the assembly method opposing arms 22 and 24 are drawn together along the y-axis, as shown in FIG. 2. Septum actuator 120 is then positioned over outer surface 36 of post 30 preparatory to being inserted within catheter adapter 130. Septum actuator 120 is inserted within catheter adapter 130 as clamp 20 is moved along x-axis 42 in a distal direction 46, as shown in FIG. 3.

In some embodiments, the position of catheter adapter 130 is held constant by securing adapter 130 in a vise or other clamp-like device (not shown). In other embodiments, catheter adapter 130 is held in a vise or other clamp-like device capable of movement along x-axis 42. Further, in some embodiments clamp 20 is limited to movement along y-axis 44, and catheter adapter 130 is limited to movement along x-axis 42. Thus, in some embodiments the method of assembly is accomplished by coordinating the movements of clamp 20 and catheter adapter 130 relative to one another.

In some embodiments, catheter adapter 130 comprises a catheter hub 132 having a lumen 134 for housing a septum 140. Septum 140 is generally provided to divide lumen 134 into a forward chamber 142 and a rearward chamber 144. In some embodiments, septum 140 is a split septum having a slit. The slit is provided as a pathway through septum 140 thereby enabling fluid communication between the forward and rearward chambers 142 and 144. In some embodiments, the slit of septum 140 is substantially closed prior to being biased open by septum actuator 120. Thus, prior to being biased open, septum 140 prevents and/or controls fluid flow between forward and rearward chambers 142 and 144. The slit of septum 140 further permits passage of introducer needle 110 without requiring needle 110 to permanently pierce septum 140.

In some embodiments, septum actuator 120 is preliminarily positioned within lumen 134 by post 30 such that actuator 120 biases the slit of septum 140 to an opened position, as shown in FIGS. 3-6. Septum actuator 120 is advanced through septum 140 by repositioning clamp 20 along x-axis 42.

In particular, in some embodiments opposing arms 22 and 24 are repositioned along the y-axis 44 to an opened position, wherein outer surface 36 of post 30 contacts an inner surface of septum actuator 120 thereby securing actuator 120 to clamp 20. Clamp 20 is then repositioned in a distal direction 46 thereby causing septum actuator 120 to be advanced through septum 140. Once positioned, opposing arms 22 and 24 are drawn together along y-axis 44 thereby causing outer surface 36 to release the inner surface of septum actuator 120, as shown in FIG. 3. Clamp 20 is then repositioned along x-axis 42 such that post 30 is withdrawn from lumen 134 and positioned over introducer needle 110, as shown in FIG. 4. Opposing arms 22 and 24 are then further drawn together to a closed position such that needle 110 is gripped and secured within groove 38 of post 30. Clamp 20 is then repositioned along x-axis 42 in a distal direction 46, as shown in FIG. 5.

Figure 5:
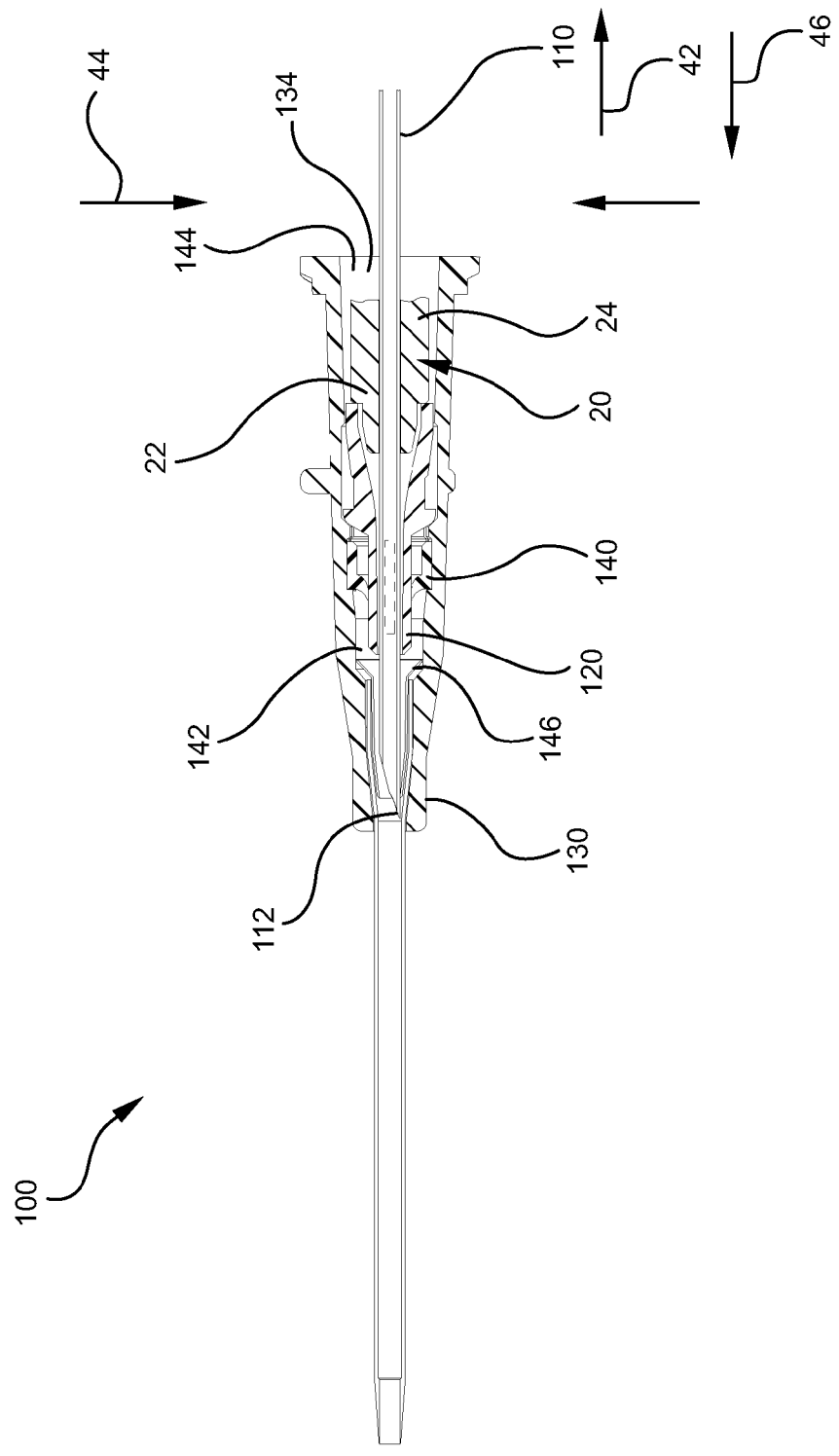
FIG. 5 is a cross-sectioned view of a catheter device and assembly system undergoing a method of assembly following the step of advancing the introducer needle through the septum via the septum actuator in accordance with a representative embodiment of the present invention.
Figure 6:
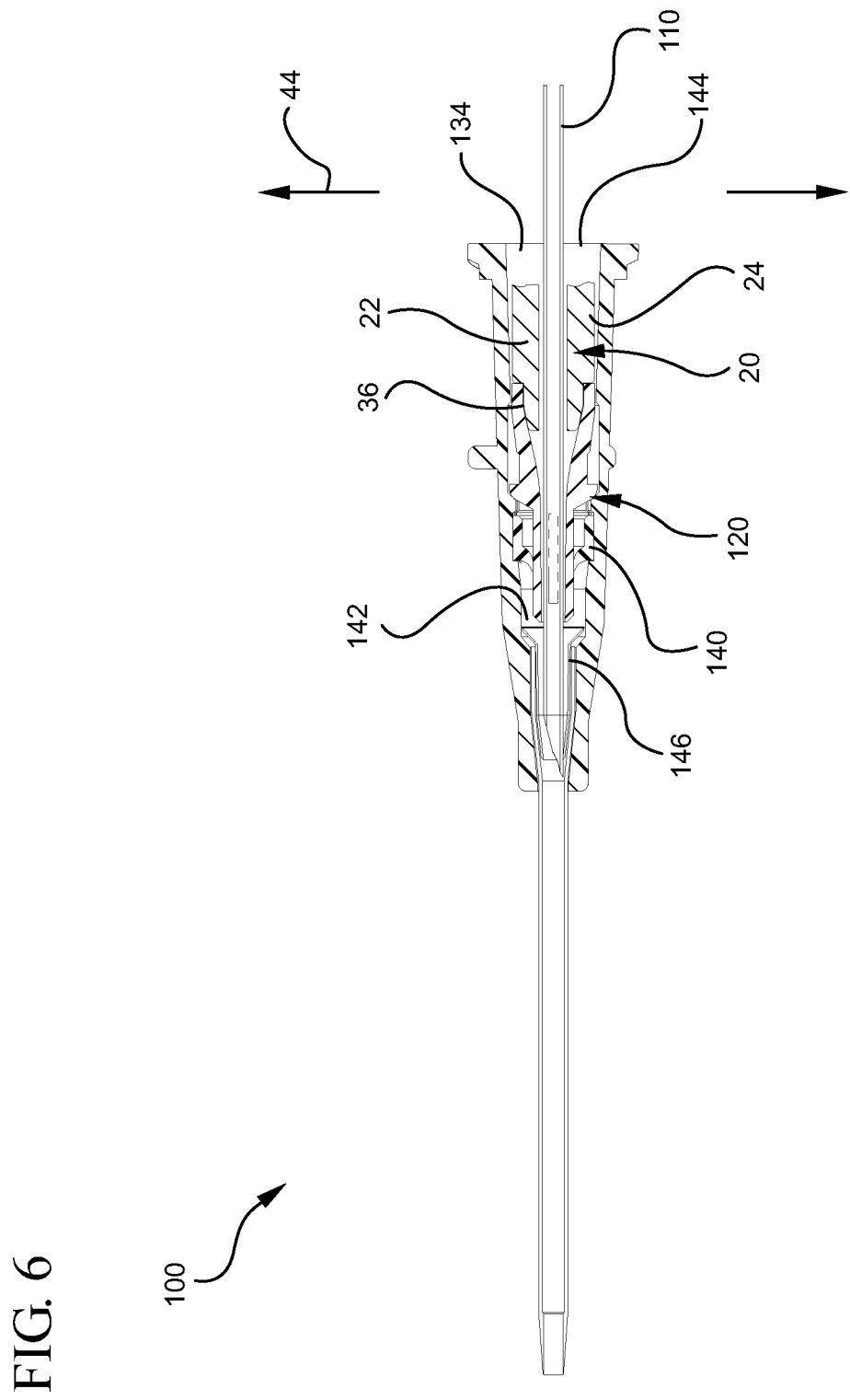
FIG. 6 is a cross-sectioned view of a catheter device and assembly system undergoing a method of assembly prior to the step of withdrawing the septum actuator from the septum in accordance with a representative embodiment the present invention.
Figure 7:
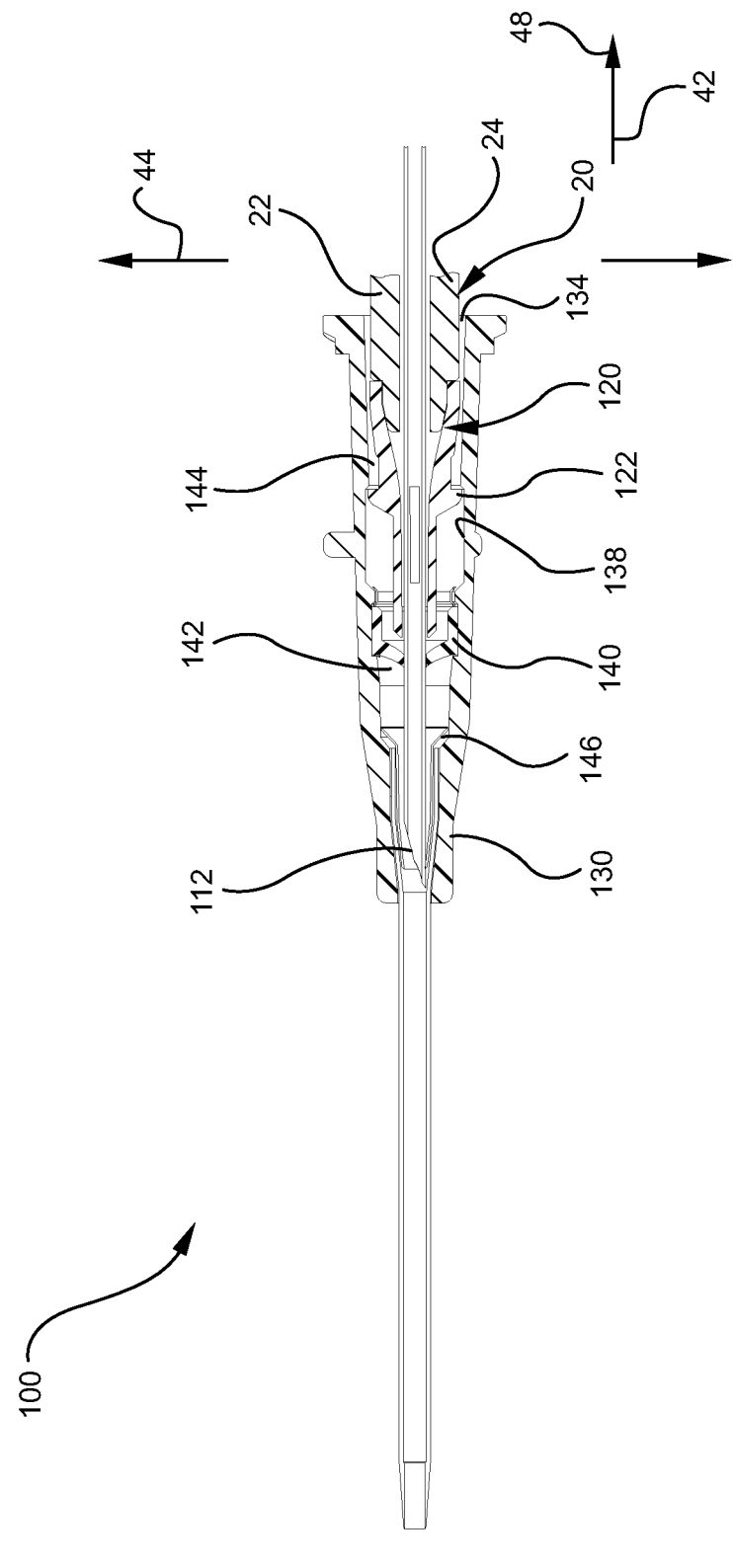
FIG. 7 is a cross-sectioned view of a catheter device and assembly system undergoing a method of assembly following the step of withdrawing the septum actuator from the septum in accordance with a representative embodiment of the present invention.

Referring now to FIG. 5, clamp 20 is advanced in a distal direction 46 such that a beveled portion 112 of needle 110 is advanced through septum 140 and into the forward chamber 142 via septum actuator 120. In some embodiments, needle 110 is advanced through septum actuator 120 such that beveled portion 112 is positioned within the wedge 146. The advanced position of septum actuator 120 provides a means whereby needle 110 is able to be inserted through septum 140 without damaging or otherwise compromising septum 140. Opposing arms 22 and 24 are then drawn apart to the opened position to reestablish contact between outer surface 36 of post 30 and the inner surface of septum actuator 120, as shown in FIG. 6. Clamp 20 is then repositioned along the x-axis 42 in a proximal direction 48 such that septum actuator 120 is withdrawn from the slit of septum 140, as shown in FIG. 7. In some embodiments, catheter adapter 130 further comprises an annular groove or channel 138 that receives a fin or outward protrusion 122 of septum actuator 120. As such, the movement of actuator 120 within lumen 134 is limited to a desired range. Thus, in some embodiments clamp 20 is repositioned within channel 138 in a proximal direction 48 such that septum actuator 120 is withdrawn from septum 140.

Following withdrawal of septum actuator 120 from septum 140, opposing arms 22 and 24 are repositioned along y-axis 44 to a middle or neutral position, wherein post 30 is free from contacting either needle 110 or septum actuator 120. Clamp 20 is then further repositioned along the x-axis 42 in a proximal direction 48 such that post 30 is withdrawn from lumen 134, as shown in FIG. 8.

Figure 8:
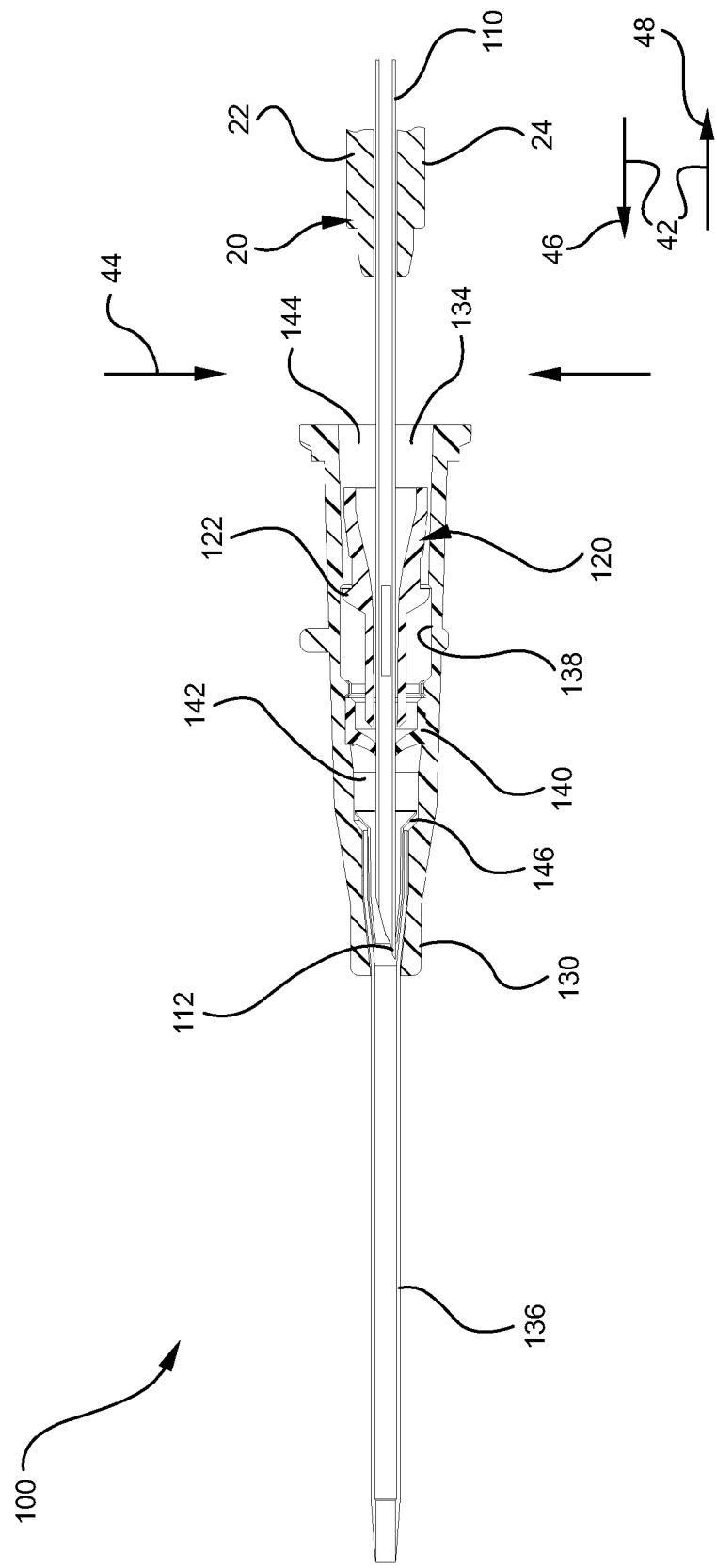
FIG. 8 is a cross-sectioned view of a catheter device and assembly system undergoing a method of assembly prior to the step of advancing the introducer needle into the catheter in accordance with a representative embodiment of the present invention.
Figure 9:
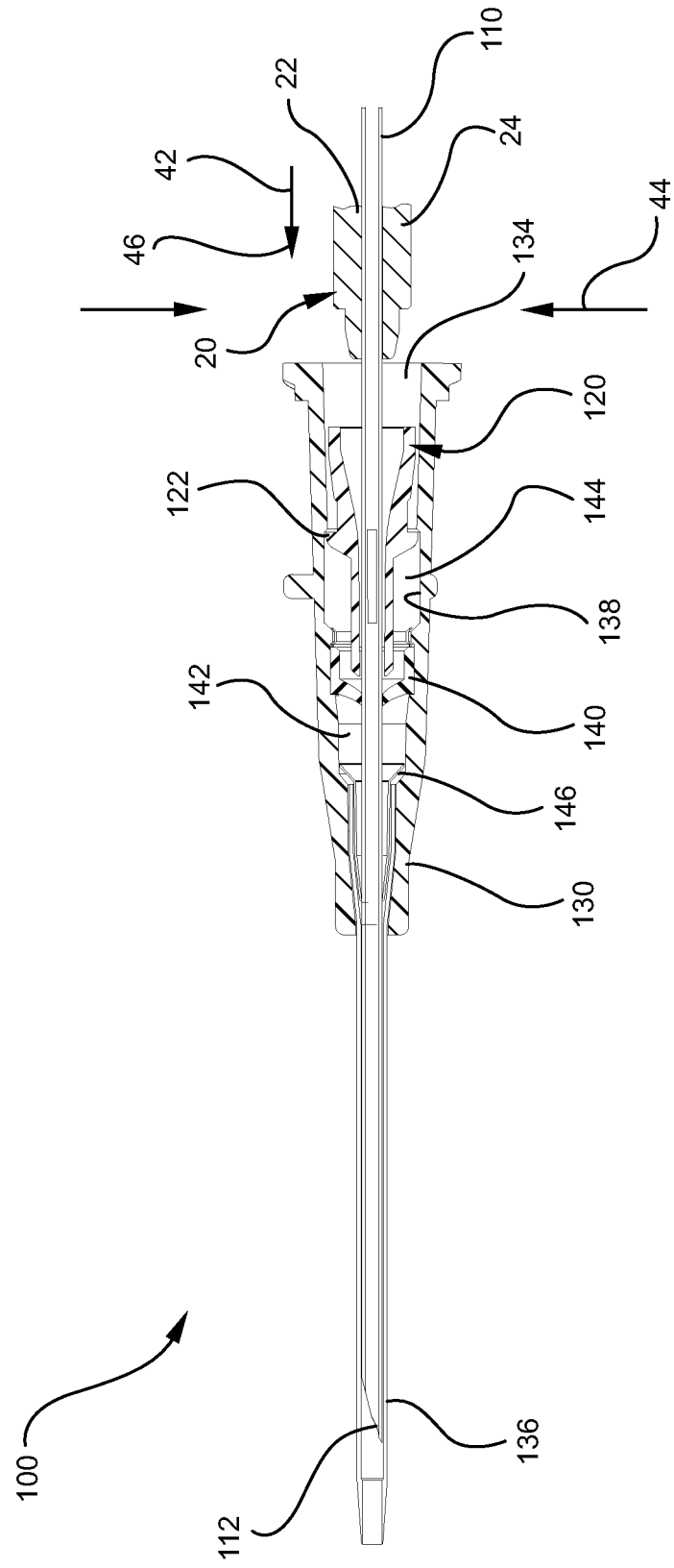
FIG. 9 is a cross-sectioned view of a catheter device and assembly system undergoing a method of assembly following the step of advancing the introducer needle into the catheter in accordance with a representative embodiment of the present invention.
Figure 10:
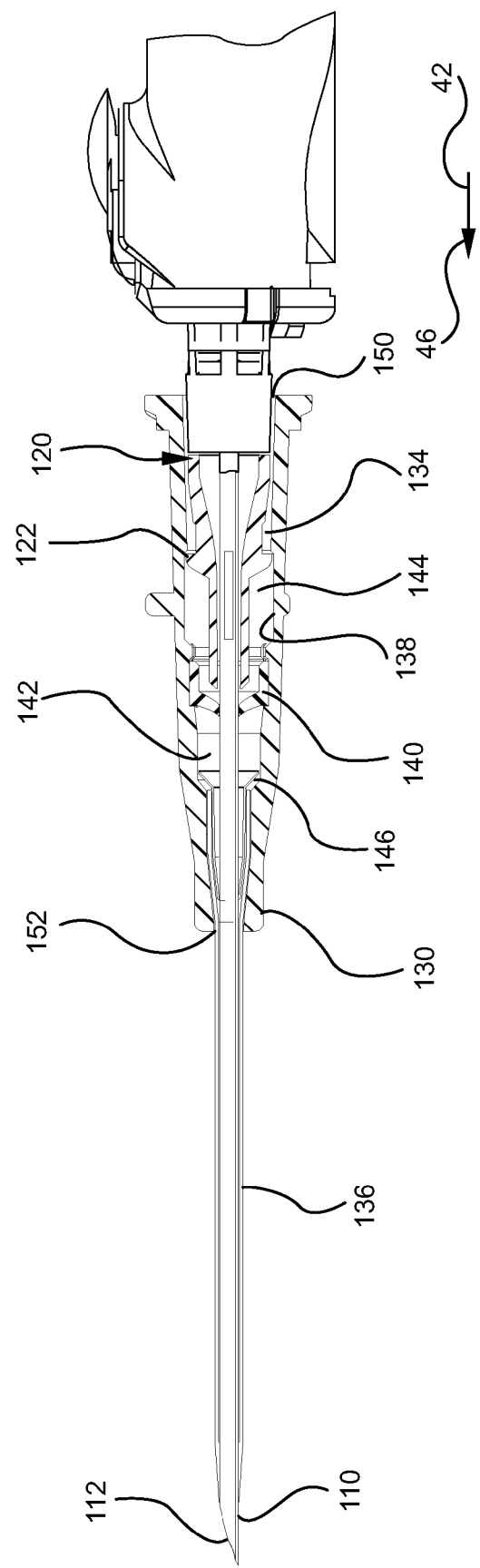
FIG. 10 is a cross-sectioned view of a catheter device and assembly system undergoing a method of assembly following the step of coupling the needle hub with the catheter hub to provide an assembled catheter device in accordance with a representative embodiment of the present invention.

With continued reference to FIG. 8, in some embodiments clamp 20 is further withdrawn from the proximity of catheter device 100, and needle 110 is advanced in a distal direction 46 through catheter 136. In other embodiments, clamp 20 is repositioned along the x-axis 42 in a proximal direction 48 and clamp onto an upstream portion of needle 110. Clamp 20 is then repositioned along the x-axis 42 in a distal direction 46 thereby further advancing needle 110 through catheter 136, as shown in FIG. 9. In some embodiments, the step of using clamp 20 to advance needle 110 through catheter 136 is repeated until beveled portion 112 is advanced to a desired position with catheter 136. In other embodiments, clamp 20 further withdrawn from the proximity of catheter device 100, and needle 110 is advanced in a distal direction 46 through catheter 136 until the catheter device 100 is fully assembled, as shown in FIG. 10.

In some methods of the present invention, a catheter device 100 is assembled by first providing a catheter adapter 130 having a proximal opening 150, a distal opening 152, and a lumen 134 extending therebetween. A catheter 136 is then swaged into the distal opening 142 of the catheter adapter, such that a lumen of the catheter 136 and lumen 134 are in fluid communication. A septum 140 is then insertedly positioned within lumen 134 thereby dividing lumen 134 into a forward chamber 142 and a rearward chamber 144.

The catheter device 100 is further assembled by insertedly positioning a septum actuator 120 through the septum 140 according to the method outlined above. For example, in some methods a clamp 20 is used to access and insertedly position the septum actuator 120 within the septum 140. The clamp 20 generally comprises an opened position, a closed position, and a middle position whereby the clamp 20 is capable of gripping the septum actuator 120 and an introducer needle 110 of the catheter device 100.

In some methods, clamp 20 is first used to grip and advance septum actuator 120 through septum 140. Clamp 20 then releases septum actuator 120 and grips introducer needle 110. Clamp 20 then advances needle 110 into lumen 134 such that a beveled tip 112 of needle 110 bypasses septum 140 via septum actuator 120 and into the forward chamber 142. In some methods, a step of adding a lubricant to the tip 112 of needle 110 is performed prior to advancing needle 110 into lumen 134. Thus, in some methods clamp 20 grips needle 110 at position proximate to a lubricated tip portion of needle 110.

Following insertion of needle tip 112, clamp 20 is then moved to the opened position whereby clamp 20 releases needle 110 and secures the inner surface of septum actuator 120. Clamp 20 is then withdrawn in a proximal direction 48 thereby removing septum actuator 120 from septum 140, such that septum actuator 120 is entirely positioned within the rearward chamber 144. Clamp 20 is then moved to the middle position such that the clamp 20 is free from contacting either the septum actuator 120 or the needle 110. While in the middle position, clamp 20 is withdrawn from lumen 134 and removed entirely from the catheter device 100. The needle 110 is then completely advanced within catheter 136 thereby completing the assembly of the catheter device 100.

In some methods, the step of withdrawing clamp 20 from lumen 134 further comprises the step of repositioning clamp 20 to the closed position so as to grip a proximal portion of needle 110. Clamp 20 is then repositioned in a distal direction 46 whereby the beveled tip 112 of needle 110 is further advanced through the forward chamber 142 and into catheter 136. Clamp 20 is then moved to the middle position and withdrawn from lumen 134.

Figure 11:
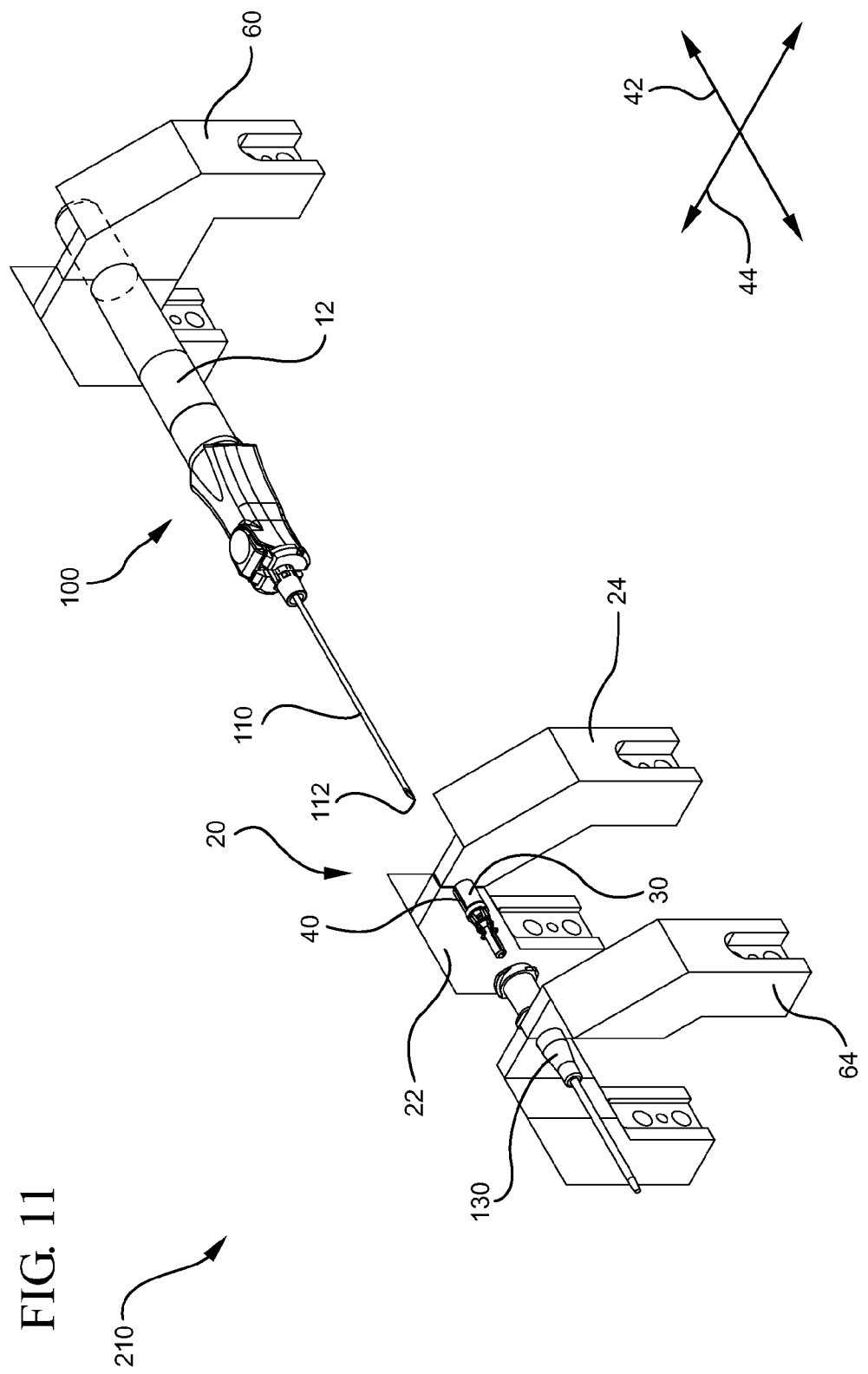
FIG. 11 is a perspective view of a catheter device and assembly system prior to undergoing a method of assembly in accordance with a representative embodiment of the present invention.

Referring now to FIG. 11, in some embodiments assembly system 210 further comprises a stationary clamp 60. Stationary clamp 60 is provided as means whereby to grip and hold needle adapter 12 during the assembly process. In some embodiments, stationary clamp 60 is mechanically connected to an automation system of actuators and gears (not shown) whereby clamp 60 is selectively repositioned along axis 42 and axis 44.

Assembly system 210 further includes a catheter adapter manipulator 64 and a septum actuator manipulator 20, or clamp, as previously discussed. Manipulator 64 is provided as means whereby to grip and hold catheter adapter 130 during the assembly process. Manipulator 64 is mechanically connected to an automation system of actuators and gears (not shown) whereby manipulator 64 is selectively repositioned along axis 42 and axis 44. In some embodiments, manipulator 64 is fixedly positioned such that catheter adapter 130 is maintained in a stationary position throughout the assembly process. For example, in some assembly processes manipulator 64 maintains a stationary position of catheter adapter 130 while clamp 20 and clamp 60 are selectively repositioned along axis 42 and axis 44 to assemble the various components of catheter device 100.

Figure 12:
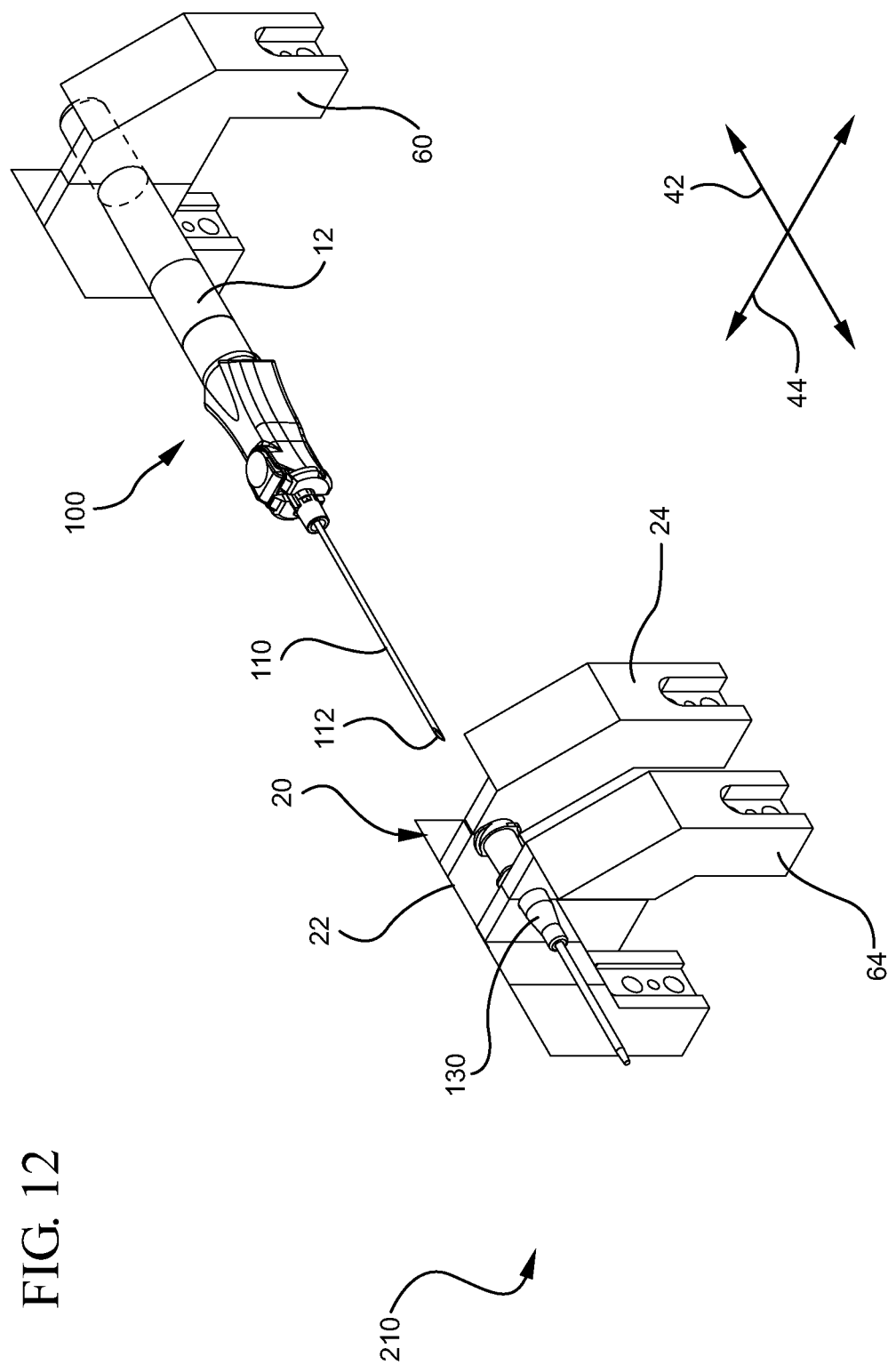
FIG. 12 is a perspective view of a catheter device and assembly system following insertion of the septum actuator into the catheter adapter as part of a method of assembly in accordance with a representative embodiment of the present invention.

Referring now to FIG. 12, an assembly system 210 is shown wherein clamp 60 is a stationary clamp, and clamps 20 and 64 are selectively repositioned along axis 42. A first step of assembly system 210 is to insert septum actuator 120 into catheter adapter 130. This first step is accomplished by selectively repositioning at least one of clamp 20 and clamp 64 such that septum actuator 120 is inserted into catheter adapter 130. Septum actuator 120 is held by clamp 20 by positioning first and second halves 22 and 24 into an open position. Septum actuator 120 is inserted within catheter adapter 130 until septum actuator 120 is advance through septum 140, thereby providing a pathway through septum 140.

Figure 13:
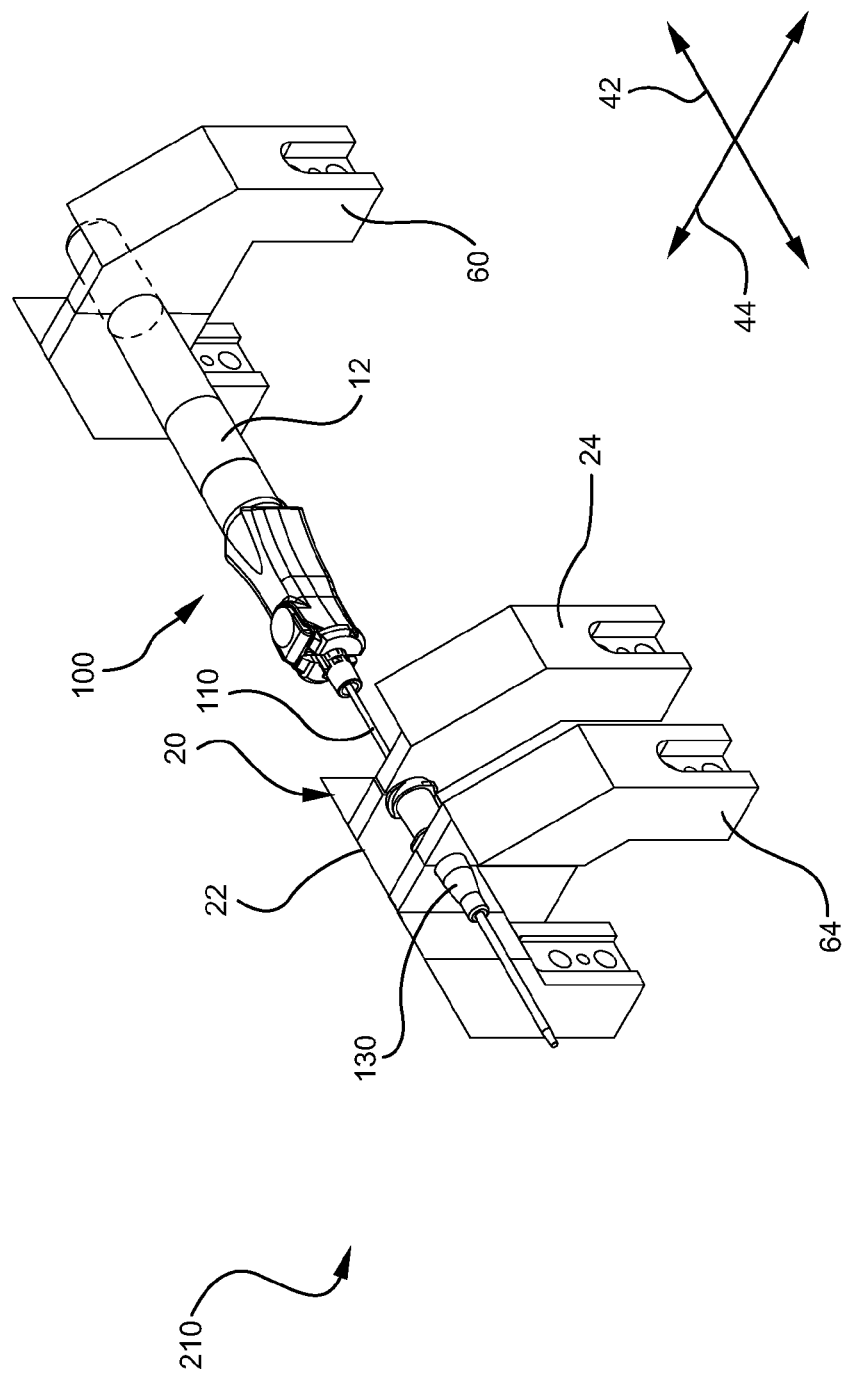
FIG. 13 is a perspective view of a catheter device and assembly system following partial insertion of the introducer needle into the catheter adapter as part of a method of assembly in accordance with a representative embodiment of the present invention.

A second step of assembly system 210 is to partially insert needle 110 through septum actuator 120 and into wedge 146 of catheter adapter 130, as shown in FIG. 13. Having positioned the septum actuator 120 through septum 140, needle 110 may now safely bypass septum 140 without puncturing or otherwise damaging septum 140.

Figure 14:
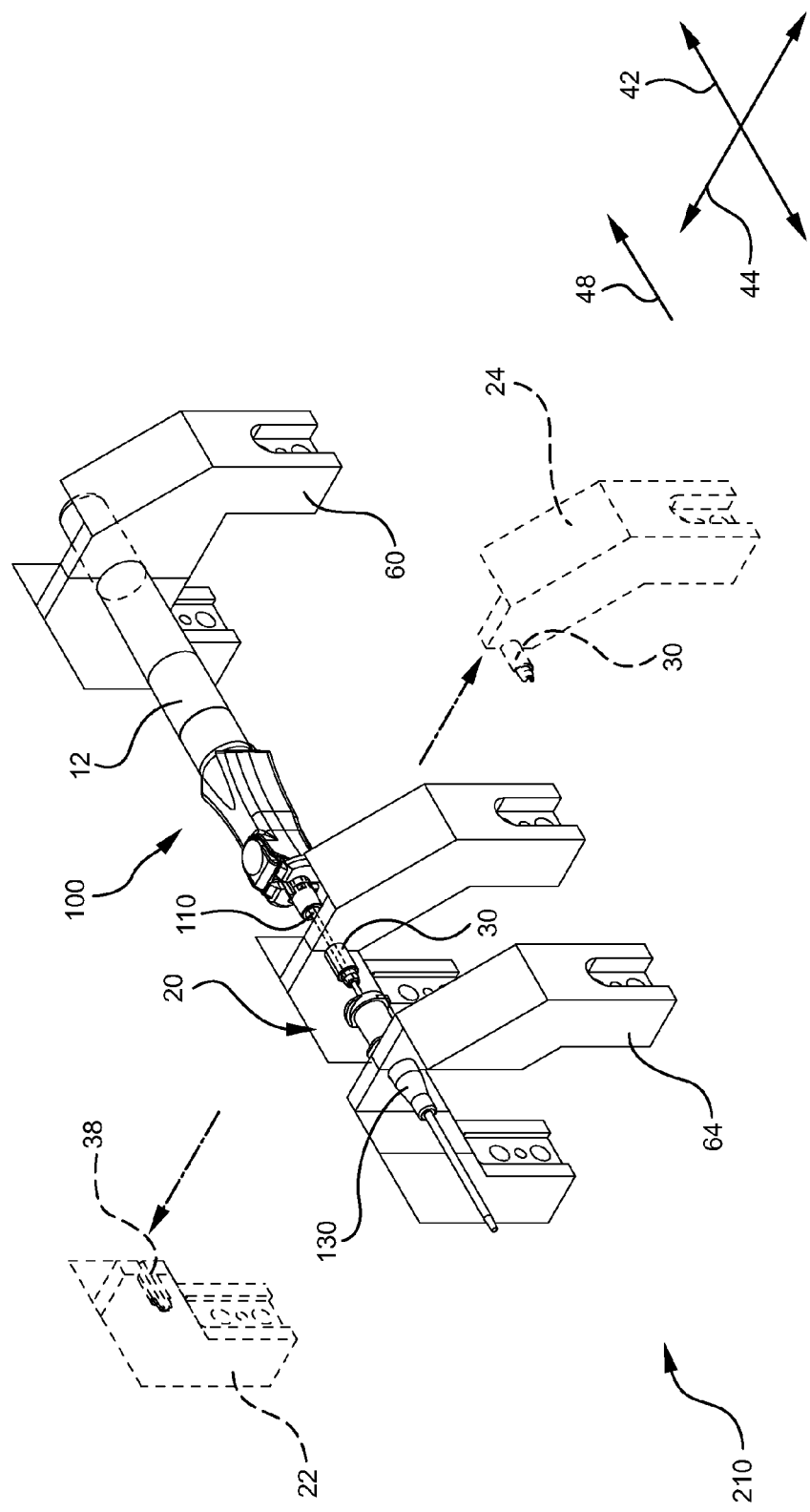
FIG. 14 is a perspective view of a catheter device and assembly system demonstrating removal of the septum actuator manipulator as part of a method of assembly in accordance with a representative embodiment of the present invention.
Figure 15:
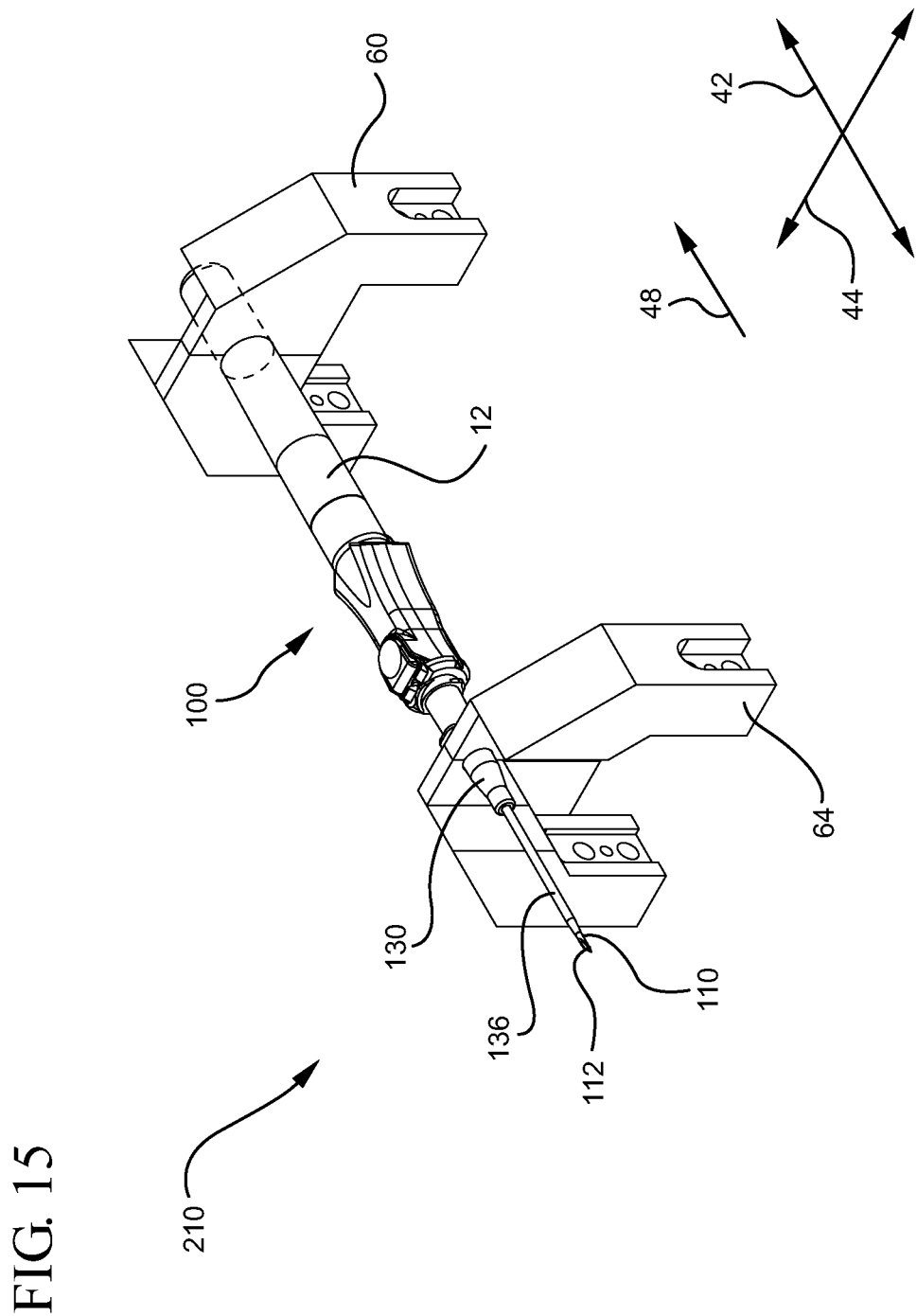
FIG. 15 is a perspective view of a catheter device and assembly system following full insertion of the introducer needle in the catheter adapter as part of a method of assembly in accordance with a representative embodiment of the present invention.

Once needle 110 is positioned within catheter adapter 130, clamp 20 is moved in a proximal direction 48 to remove septum actuator 120 from septum 140, and position septum actuator 120 just proximal to septum 140. Clamp 20 is then moved to a closed position and repositioned in a proximal direction 48, as shown in FIG. 14. In some embodiments, groove 38 of clamp 20 comprises a diameter greater than the outer diameter of introducer needle 110. This feature allows clamp 20 to be repositioned relative to needle 110 while in the closed position. Once post 30 has cleared catheter adapter 130, clamp 20 is removed from needle 110, as shown. Clamp 64 is then repositioned in a proximal direction 48 thereby fully advancing needle 110 through catheter adapter 130 and catheter 136, such that needle 110 extends distally beyond catheter 136, as shown in FIG. 15. The final step is to remove clamp 64 and stationary clamp 60 from assembled catheter device 100.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A device for insertedly positioning a needle within a catheter assembly, the catheter assembly comprising a catheter coupled to a catheter adapter, the catheter assembly further comprising a septum disposed within a lumen of the catheter adapter, and a septum actuator disposed within the lumen so as to provide a pathway through the septum, the device comprising:

a clamp having a closed position and an open position, the clamp further having an inner surface for selectively retaining a needle, and an outer surface for selectively contacting an inner surface of the septum actuator to facilitate insertion and withdrawal the septum actuator from the septum thereby selectively providing the pathway through the septum, wherein the needle is secured by the clamp in the closed position, the clamp and the needle thereafter being inserted into the catheter assembly such that a tip of the needle is passed through the septum via the pathway provided by the septum actuator, the outer surface of the clamp being coaxially positioned within the septum actuator, the clamp thereafter being repositioned to the open position whereby the needle is released by the clamp and the outer surface of the clamp contacts the inner surface of the septum actuator, the clamp and septum actuator thereafter being moved in a proximal direction such that the septum actuator is removed from within the pathway of septum, the clamp then being repositioned to the middle position such that neither the needle nor the septum actuator are contacted by the clamp, the clamp then being moved further in a the proximal direction such that the clamp is entirely removed from the catheter assembly and needle.

2. The device of claim 1, wherein an outer diameter of the clamp coaxially centers the needle and the clamp within the septum actuator.

3. The device of claim 1, wherein a tip portion of the needle further comprises a lubricant coating.

4. The device of claim 1, wherein the outer surface is tapered.

5. The device of claim 2, wherein the outer diameter is less than an inner diameter of the catheter adapter yet greater than an inner diameter of the septum actuator.

6. The device of claim 1 further comprising an automation system mechanically coupled to the clamp, wherein the automation system controls the positions of the clamp relative to the needle and the catheter assembly.

* * * * *